(12) United States Patent
Auerbach et al.

(10) Patent No.: US 8,979,747 B2
(45) Date of Patent: Mar. 17, 2015

(54) ENDOSCOPIC PORTS AND RELATED KITS AND METHODS

(75) Inventors: Robert D. Auerbach, Madison, CT (US); Charles Sherts, Westport, CT (US); Robert Williams, Norwalk, CT (US)

(73) Assignee: Cooper Surgicalk, Inc., Trumbull, CT (US)

( * ) Notice: Subject to any disclaimer, the term of this patent is extended or adjusted under 35 U.S.C. 154(b) by 269 days.

(21) Appl. No.: 13/555,660

(22) Filed: Jul. 23, 2012

(65) Prior Publication Data

US 2013/0079597 A1 Mar. 28, 2013

Related U.S. Application Data

(60) Provisional application No. 61/538,239, filed on Sep. 23, 2011.

(51) Int. Cl.
| | | |
|---|---|---|
| A61B 17/34 | (2006.01) | |
| A61B 17/02 | (2006.01) | |
| A61B 17/04 | (2006.01) | |
| A61B 17/00 | (2006.01) | |
| A61B 17/06 | (2006.01) | |

(52) U.S. Cl.
CPC ............ *A61B 17/3423* (2013.01); *A61B 17/02* (2013.01); *A61B 17/0482* (2013.01); *A61B 2017/3445* (2013.01); *A61B 2017/00637* (2013.01); *A61B 17/0057* (2013.01); *A61B 17/06109* (2013.01); *A61B 2017/00663* (2013.01); *A61B 2017/06042* (2013.01); *A61B 17/3462* (2013.01); *A61B 17/3474* (2013.01)
USPC ...................................................... 600/204

(58) Field of Classification Search
USPC ......... 600/201, 203, 206, 208, 204, 205, 210, 600/215, 235, 202, 207, 209, 213; 604/158–161, 164.01, 164.04, 164.06, 604/164.07, 166.01
See application file for complete search history.

(56) References Cited

U.S. PATENT DOCUMENTS

| | | | | |
|---|---|---|---|---|
| 3,817,251 | A | * | 6/1974 | Hasson ............................ 604/26 |
| 4,089,337 | A | * | 5/1978 | Kronner ................... 604/103.03 |
| 4,861,334 | A | * | 8/1989 | Nawaz .......................... 604/539 |

(Continued)

FOREIGN PATENT DOCUMENTS

| | | |
|---|---|---|
| EP | 2 305 129 | 4/2011 |
| EP | 2 412 317 | 2/2012 |

(Continued)

OTHER PUBLICATIONS

CooperSurgical, "Carter-Thomason CloseSure System," pp. 1-6; Oct. 2010.

(Continued)

*Primary Examiner* — Michael T Schaper
*Assistant Examiner* — Amy Sipp
(74) *Attorney, Agent, or Firm* — Fish & Richardson P.C.

(57) ABSTRACT

An endoscopic port that includes an elongate cannula defining a central lumen that extends substantially parallel to a longitudinal axis of the cannula and is sized to receive at least one endoscopic instrument therein. The cannula further defines a first opening that extends through a sidewall of the cannula at an acute angle relative to the longitudinal axis of the cannula. The first opening is sized to receive a suture passer.

26 Claims, 13 Drawing Sheets

(56) References Cited

U.S. PATENT DOCUMENTS

| | | | |
|---|---|---|---|
| 5,002,557 A * | 3/1991 | Hasson | 606/191 |
| 5,197,971 A | 3/1993 | Bonutti | |
| 5,269,772 A | 12/1993 | Wilk | |
| 5,372,583 A * | 12/1994 | Roberts et al. | 604/506 |
| 5,496,335 A * | 3/1996 | Thomason et al. | 606/148 |
| 5,501,692 A * | 3/1996 | Riza | 606/148 |
| 5,507,758 A * | 4/1996 | Thomason et al. | 606/148 |
| 5,716,369 A * | 2/1998 | Riza | 606/148 |
| 5,882,344 A * | 3/1999 | Stouder, Jr. | 604/264 |
| 5,993,471 A * | 11/1999 | Riza et al. | 606/185 |
| 6,142,931 A | 11/2000 | Kaji | |
| 6,183,485 B1 * | 2/2001 | Thomason et al. | 606/148 |
| 6,197,002 B1 * | 3/2001 | Peterson | 604/164.01 |
| 6,203,554 B1 | 3/2001 | Roberts | |
| 6,783,516 B2 | 8/2004 | O'Heeron et al. | |
| 6,830,578 B2 | 12/2004 | O'Heeron et al. | |
| 2003/0158572 A1 * | 8/2003 | McFarlane | 606/192 |
| 2004/0087978 A1 * | 5/2004 | Velez et al. | 606/144 |
| 2006/0025749 A1 | 2/2006 | Moenning | |
| 2006/0030868 A1 | 2/2006 | Bennett, III | |
| 2007/0191772 A1 * | 8/2007 | Wojcik | 604/158 |
| 2007/0203507 A1 | 8/2007 | McLaughlin et al. | |
| 2008/0033459 A1 | 2/2008 | Shafi et al. | |
| 2008/0086165 A1 * | 4/2008 | Lyon et al. | 606/191 |
| 2008/0097485 A1 * | 4/2008 | Shpaichler et al. | 606/148 |
| 2010/0280327 A1 * | 11/2010 | Nobis et al. | 600/210 |
| 2011/0021880 A1 * | 1/2011 | Okoniewski | 600/215 |
| 2011/0112557 A1 * | 5/2011 | Beeley | 606/148 |
| 2011/0237901 A1 * | 9/2011 | Duke et al. | 600/208 |
| 2012/0029532 A1 | 2/2012 | Hodgkinson et al. | |
| 2012/0035623 A1 * | 2/2012 | Bagaoisan et al. | 606/144 |
| 2012/0165611 A1 * | 6/2012 | Warren et al. | 600/204 |
| 2012/0238823 A1 * | 9/2012 | Hagerty et al. | 600/206 |
| 2012/0265223 A1 * | 10/2012 | Shpaichler et al. | 606/148 |
| 2014/0163323 A1 * | 6/2014 | Mohajer-Shojaee | 600/204 |

FOREIGN PATENT DOCUMENTS

| | | | |
|---|---|---|---|
| WO | WO 98/22040 | 5/1998 | A61F 2/00 |
| WO | WO 2006/111955 | 10/2006 | |
| WO | WO 2007/000159 | 1/2007 | |
| WO | WO 2009/031991 | 3/2009 | |
| WO | WO 2009/138839 | 11/2009 | |
| WO | WO 2010/000033 | 1/2010 | |
| WO | WO 2010/081096 | 7/2010 | |
| WO | WO 2013/019370 | 2/2013 | |

OTHER PUBLICATIONS

CooperSurgical; "Marlow Balloon Cannula with Atraumatic Surface Disc," pp. 1-2, Sep. 1997.

Dr. A H Beeley, "The Beeley Trocar Brochure—Port Site Suture System Trocar," Society of Laparoendoscopic Surgeons, www.pssstlaparoscopy.com, pp. 2, 2011.

Elashry et al., "Comparative Clinical Study of Port-Closure Techniques Following Laparoscopic Surgery," Journal of the American College of Surgeons, vol. 183, pp. 335-344, Oct. 1996.

International Search Report and Written Opinion; Application No. PCT/US2012/047823; mailed Oct. 11, 2012.

International Preliminary Report on Patentability and Written Opinion for International Application No. PCT/US2012/047823 dated Apr. 3, 2014 (9 pages).

* cited by examiner

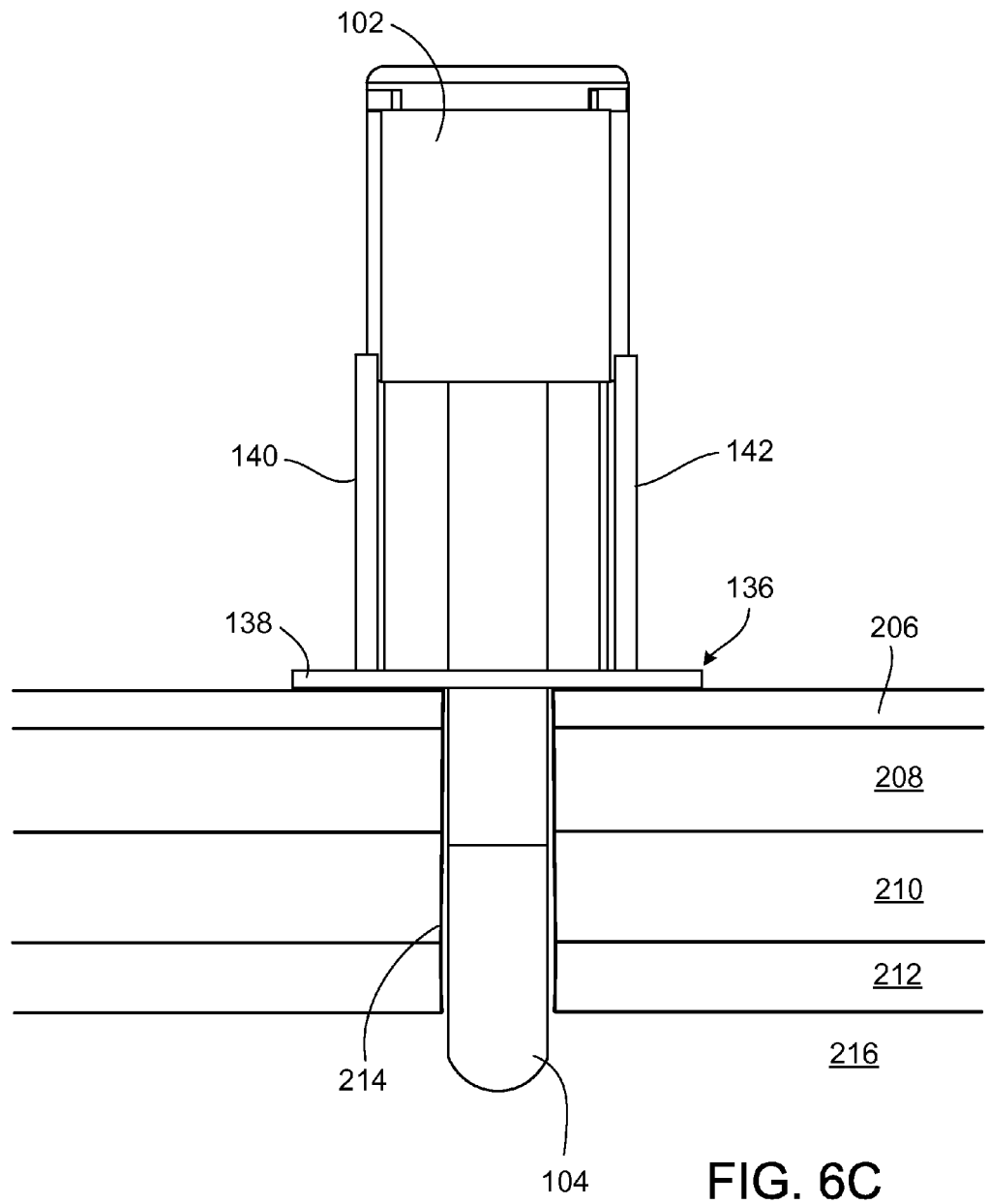

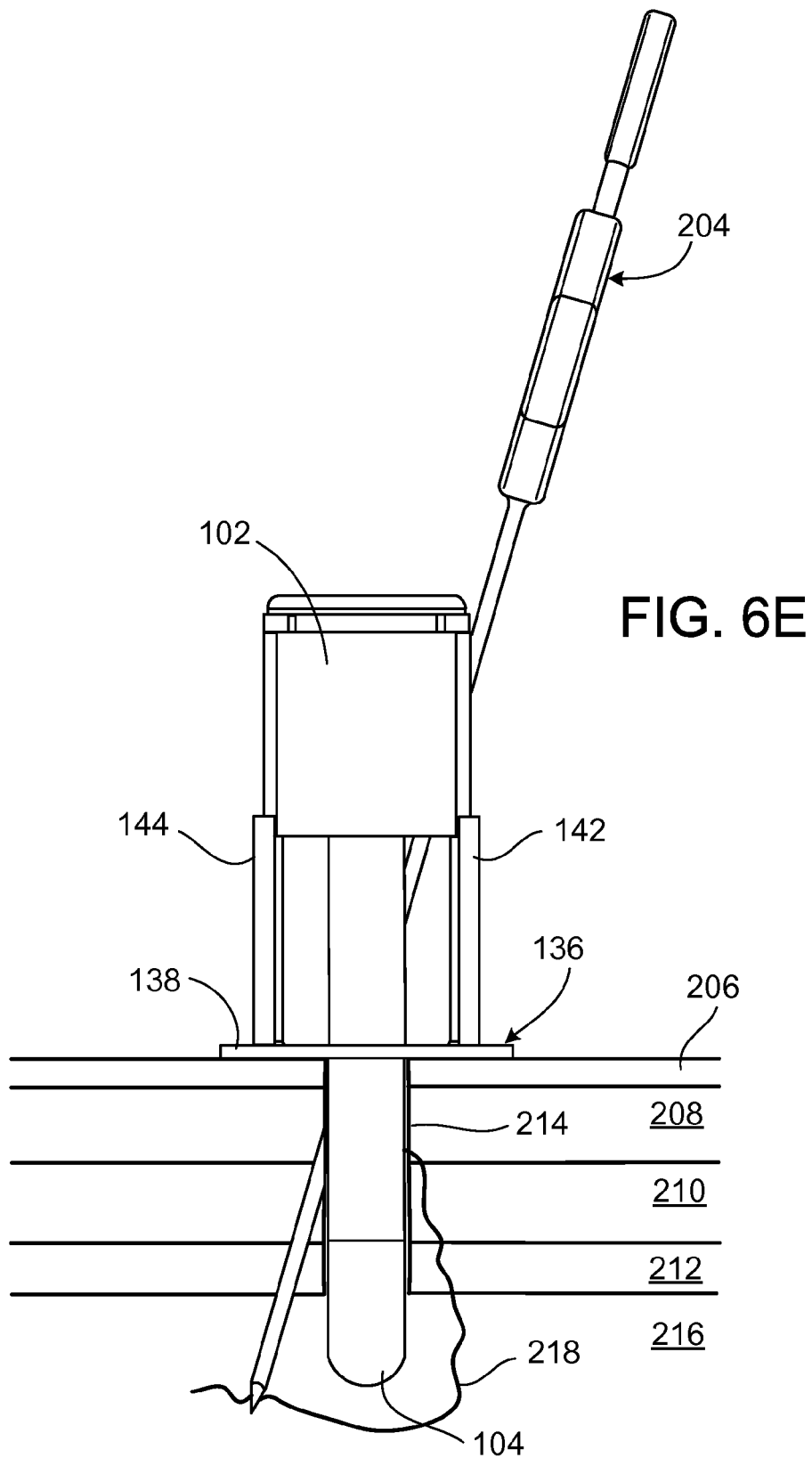

ENDOSCOPIC PORTS AND RELATED KITS AND METHODS

CROSS-REFERENCE TO RELATED APPLICATIONS

This application claims the benefit of U.S. Provisional Application Ser. No. 61/538,239, filed on Sep. 23, 2011, which is incorporated by reference herein.

TECHNICAL FIELD

This disclosure relates to endoscopic ports and related kits and methods.

BACKGROUND

Endoscopic ports (e.g., laparoscopic ports) are medical devices through which surgical instruments can be inserted into a surgical cavity (e.g., the abdominal cavity) of a patient during endoscopic surgical procedures (e.g., laparoscopic surgical procedures). To insert an endoscopic port into a surgical cavity of a patient, an obturator is typically positioned within the endoscopic port such that a sharp piercing tip of the obturator extends beyond the distal end of the endoscopic port, and then the endoscopic port and the obturator (often referred to in combination as a trocar) are pushed through the wall of the surgical cavity until the sharp tip of the obturator and the distal end of the of the endoscopic port are positioned within the surgical cavity. The sharp tip of the obturator serves to puncture the wall and facilitate the passage of the endoscopic port through the wall. Typically, after insertion of the endoscopic port and obturator through the wall, the obturator is removed by the surgeon, leaving the endoscopic port protruding through the wall into the surgical cavity. Cameras and other surgical instruments can then be inserted through the endoscopic port to view internal organs and to perform surgical procedures within the cavity. In many cases, after completing the surgical procedure, a suture is used to repair the puncture wound created in the tissue of the patient by the endoscopic port and the obturator.

SUMMARY

In one aspect of the invention, an endoscopic port includes an elongate cannula defining a central lumen that extends substantially parallel to a longitudinal axis of the cannula and is sized to receive at least one surgical instrument A sidewall of the cannula defines a first opening that extends at an acute angle relative to the longitudinal axis of the cannula and is sized to receive a suture passer.

In another aspect of the invention, an endoscopic port includes an elongate cannula defining a central lumen that extends substantially parallel to a longitudinal axis of the cannula and is sized to receive at least one surgical instrument. A sidewall of the cannula defines first and second openings that are longitudinally spaced apart along the cannula and extend through the sidewall of the cannula at an acute angle relative to the longitudinal axis of the cannula. The first and second openings are sized to receive a suture passer.

In an additional aspect of the invention, an endoscopic surgical kit includes a suture passer and an endoscopic port. The endoscopic port includes an elongate cannula defining a central lumen that extends substantially parallel to a longitudinal axis of the cannula and is sized to receive a surgical instrument. A sidewall of the cannula defines a first opening that extends through the sidewall of the cannula at an acute angle relative to the longitudinal axis of the cannula and is sized to receive the suture passer.

In a further aspect of the invention, a method includes inserting an endoscopic port including an obturator disposed within a central lumen of a cannula into a patient, thereby forming a puncture wound, removing the obturator from the central lumen of the cannula, and with the endoscopic port disposed within the puncture wound, passing a suture through the endoscopic port and through tissue of the patient adjacent the endoscopic port.

Embodiments can include one or more of the following features.

In some embodiments, the sidewall of the cannula further defines a second opening that is longitudinally spaced from the first opening and extends at an acute angle relative to the longitudinal axis of the cannula. The first and second openings are aligned so that a suture passer can be simultaneously disposed within the first and second openings.

In certain embodiments, the sidewall of the cannula further defines third and fourth openings that are longitudinally spaced from one another and extend at an acute angle relative to the longitudinal axis of the cannula. The third and fourth openings are aligned so that a suture passer can be simultaneously disposed within the third and fourth openings.

In some embodiments, each of the first, second, third, and fourth openings extends at substantially the same angle relative to the longitudinal axis.

In certain embodiments, the first opening extends through the sidewall of the cannula at an angle of 8 degrees to 30 degrees (e.g., 12 degrees to 25 degrees, 16 degrees to 20 degrees, 20 degrees, 25 degrees) relative to the longitudinal axis.

In some embodiments, the endoscopic port further includes a stop member secured to the cannula and having a width greater than the cannula.

In certain embodiments, the stop member has a substantially flat surface configured to abut an outer skin surface of a patient when the endoscopic port is inserted into a surgical cavity of the patient.

In some embodiments, a distance between the flat surface of the stop member and a distal tip of the endoscopic port is greater than a distance between the outer skin surface of the patient and the surgical cavity.

In certain embodiments, the distance between the flat surface of the stop member and the distal tip of the endoscopic port is about 3.0 cm to about 10 cm greater than the distance between the outer skin surface of the patient and the surgical cavity.

In some embodiments, the stop member is a ring having a diameter greater than an outer diameter of the cannula.

In certain embodiments, the diameter of the ring is about 1.5 times to about 4.0 times greater than the outer diameter of the cannula.

In some embodiments, the stop member is displaceable between a proximal position and a distal position.

In certain embodiments, the stop member covers the first opening when the stop member is in the proximal position and the stop member does not cover the first opening when the stop member is in the distal position.

In some embodiments, a distance between a distal surface of the stop member and a distal tip of the endoscopic port is greater than a distance between an outer skin surface of a patient and a surgical cavity into which the endoscopic port is to be inserted.

In certain embodiments, the stop member is configured to be releasably locked in the proximal and distal positions.

In some embodiments, the stop member includes a projection and the endoscopic port defines proximal and distal depressions configured to receive the projection when the stop member is in the proximal and distal positions, respectively.

In certain embodiments, the depressions are formed in a seal housing attached to a proximal end region of the cannula.

In some embodiments, the stop member includes a resilient tab from which the projection extends.

In certain embodiments, the stop member is axially displaceable between the proximal and distal positions.

In some embodiments, the stop member is pivotable between the proximal and distal positions.

In certain embodiments, the stop member is pivotably secured to a seal housing attached to a proximal end region of the cannula.

In some embodiments, the stop member is a c-shaped member defining a void that is arranged to receive the cannula when the stop member is in the distal position.

In certain embodiments, the endoscopic port defines a second opening that is longitudinally spaced from the first opening and extends at an acute angle relative to the longitudinal axis of the cannula. The first and second openings are aligned so that a suture passer can be simultaneously disposed within the first and second openings.

In some embodiments, the sidewall of the cannula further defines a third opening that extends at an acute angle relative to the longitudinal axis of the cannula. The third opening is sized to receive a suture passer.

In certain embodiments, the endoscopic port defines a fourth opening that is longitudinally spaced from the third opening and extends at an acute angle relative to the longitudinal axis of the cannula. The third and fourth openings are aligned so that a suture passer can be simultaneously disposed within the third and fourth openings.

In some embodiments, each of the first, second, third, and fourth openings are defined by the sidewall of the cannula.

In certain embodiments, the first, second, third, and fourth openings are configured so that a first suture passer can be disposed within the first second openings while a second suture passer is disposed within the third and fourth openings.

In some embodiments, the second opening is defined by the cannula.

In certain embodiments, the second opening is defined by a member secured to a proximal end region of the cannula.

In some embodiments, the member is a guide plug that is disposed within a seal housing secured to a proximal end region of the cannula.

In certain embodiments, the guide plug is configured to be disposed in a seal in the seal housing.

In some embodiments, the guide plug and a seal are interchangeably disposed within the seal housing.

In certain embodiments, the member is a guide stem that is disposed atop a platform that is rotatably secured to the cannula.

In some embodiments, the guide stem defines a guide channel that aligns with the first opening.

In certain embodiments, the endoscopic port further includes a seal housing positioned atop the platform such that the seal housing and the guide stem can be interchangeably aligned with the cannula by rotating the platform relative to the cannula.

In some embodiments, the endoscopic port further includes a pierceable material secured to the cannula in a manner such that the pierceable material covers the first opening.

In certain embodiments, the pierceable material forms a fluid-tight seal with the cannula.

In some embodiments, the pierceable material is opaque.

In certain embodiments, the pierceable material has a color that is different than a color of the cannula.

In some embodiments, the central lumen of the cannula extends along the longitudinal axis.

In certain embodiments, the endoscopic port further includes a seal assembly positioned along the central lumen and configured to form a substantially fluid-tight seal around a surgical instrument when the surgical instrument is disposed within the central lumen.

In some embodiments, the seal assembly is disposed in a seal housing attached to a proximal end region of the cannula.

In certain embodiments, the endoscopic surgical kit further includes an obturator configured to be disposed within the central lumen of the cannula.

In some embodiments, the kit includes multiple differently sized endoscopic ports.

In certain embodiments, passing the suture through the endoscopic port includes grasping the suture with a suture passer and passing the suture passer and the grasped suture through a guide passageway defined by the endoscopic port.

In some embodiments, the suture is passed through the tissue of the patient and into a surgical cavity of the patient.

In certain embodiments, the method further includes pulling the suture through tissue of the patient adjacent the endoscopic port and through the endoscopic port.

In some embodiments, the method further includes passing a suture passer through a guide passageway defined by the endoscopic port and into the surgical cavity and grasping the suture with the suture passer.

In certain embodiments, pulling the suture through the tissue of the patient adjacent the endoscopic port and through the endoscopic port includes pulling the suture passer and the grasped suture through a guide passageway defined by the endoscopic port.

In some embodiments, the guide passageway through which the suture is delivered to the surgical cavity and the guide passageway though which the suture is retrieved from the surgical cavity are different passageways.

In certain embodiments, the method further includes removing the endoscopic port from the puncture wound and tying the suture to repair the puncture wound.

In some embodiments, a distal end of the endoscopic port remains disposed within a surgical cavity of the patient while passing the suture through the endoscopic port and through the tissue of the patient adjacent the endoscopic port.

In certain embodiments, the surgical cavity is an abdominal cavity.

In some embodiments, the method further includes delivering gas into a surgical cavity of the patient via the endoscopic port to pressurize the surgical cavity.

In certain embodiments, a pressure of the pressurized surgical cavity (e.g., a pressurized abdominal cavity) is maintained while the endoscopic port is disposed within the puncture wound.

In some embodiments, the method further includes inserting a surgical instrument through the central lumen of the cannula after removing the obturator.

In certain embodiments, the surgical instrument is removed from the central lumen of the cannula prior to passing the suture through the endoscopic port and through the tissue of the patient adjacent the endoscopic port.

Embodiments can include one or more of the following advantages.

In certain embodiments, the endoscopic port is designed to remain positioned in the puncture wound with the distal end of the endoscopic port extending into the surgical cavity of the patient while the surgeon passes a suture through the patient's tissue into the surgical cavity and then retrieves the suture from the surgical cavity to repair the puncture wound. Because there is no need to remove the endoscopic port prior to positioning the suture in this way, loss of pressurization of the surgical cavity (e.g., pneumoperitoneum) during placement of the suture can be greatly reduced or eliminated. As a result, it is typically not necessary to re-insufflate the surgical cavity and reposition endoscopic instruments disposed within the surgical cavity. Thus, the time required to perform surgical procedures using endoscopic ports described herein can be reduced compared to certain conventional procedures that require an endoscopic port to be removed from the puncture wound and then replaced with a separate guide member and that often times require re-insufflation of the surgical cavity due to the removal of the endoscopic port.

Additionally, the ability to leave the endoscopic port positioned in the puncture wound until it is time to close that wound can help to preserve the tissue surrounding the puncture wound. For example, when an endoscopic port is removed from a puncture wound only to be replaced by another device and/or to be later re-inserted into the puncture wound, damage can be caused to the tissue surrounding the puncture wound upon inserting the other device into the wound or re-inserting the endoscopic port into the wound. With certain patients, particularly obese patients, it is often times difficult to relocate the path of the original puncture wound through the various layers of adipose and other tissue. In attempting to do so, the surgeon may inadvertently puncture tissue (e.g., fascia) adjacent the original puncture wound, thereby creating an additional puncture wound. By designing the endoscopic port so that it can remain disposed in the original puncture wound throughout the procedure, the incidence of such inadvertent punctures can be reduced or eliminated.

In some embodiments, the endoscopic port is configured so that approximately the same amount of tissue is grasped by a suture on either side of the puncture wound when a suture passer is used to deliver the suture into the surgical cavity through a guide passageway that is formed at least in part by one or more openings formed in the cannula of the endoscopic port and then retrieved from the surgical cavity by pulling the suture though another guide passageway that is formed at least in part by one or more openings formed in the cannula of the endoscopic port with the suture passer. This can help to ensure a complete closure of the wound.

In certain embodiments, a member or stop that is wider (e.g., has a greater diameter) than the puncture wound created by the endoscopic port is provided along the cannula of the endoscopic port to limit the extent to which the distal end of the cannula can extend into the surgical cavity. The member can, for example, be positioned along the cannula at a point to ensure that the distal end of the cannula only slightly extends into the surgical cavity of the particular patient to be treated. Limiting the extent to which the distal end of the cannula extends into the surgical cavity facilitates suturing of the puncture wound by making it easier for the user to deliver and retrieve the suture within the surgical cavity. At the same time, ensuring that the distal end of the cannula is positioned in the surgical cavity ensures that the surgeon will not need to spend wasted time searching for the original puncture wound or re-inserting the endoscopic port prior to placement of the suture.

In some embodiments, the member or stop is moveable between a distal position and a proximal position. Positioning the member in the distal position ensures that the distal end of the cannula protrudes only slightly into the surgical cavity and thus facilitates placement of the suture, while positioning the member in the proximal position allows the distal end of the cannula to be inserted further into the surgical and thus permits access to a larger portion of the surgical cavity with surgical instruments fed through the endoscopic port.

In certain embodiments, the endoscopic port is equipped with a film or other pierceable material positioned over the opening(s) in the side wall of the cannula. This arrangement helps to ensure that the cannula is able to provide a substantially fluid-tight barrier along its length, including in the area of the opening(s). This arrangement, therefore, helps to maintain a desired pressure within a pressurized surgical cavity (e.g., a pneumoperitoneum) during a surgical procedure.

In some embodiments, a seal covers the opening(s) in a manner to seal around the suture passer when the suture passer is disposed in the opening(s) and to self-seal when the suture passer has been removed from the opening(s). This arrangement helps to maintain a desired pressure within a pressurized surgical cavity (e.g., a pneumoperitoneum) throughout the entire surgical procedure.

In addition, in some embodiments, the diameter of the opening(s) in the sidewall of the cannula is approximately equal to the outer diameter of the suture passer to be used with the endoscopic port. This configuration helps to reduce (e.g., minimize) the amount of insufflation gas that can escape via the opening(s) when the suture passer is disposed within the opening(s) during a procedure.

Certain procedures require that multiple endoscopic ports be inserted into the patient. One of those endoscopic ports is typically used to insert a camera into the surgical cavity. Images produced by the camera can be used to enable the surgeon to properly grasp sutures positioned in the surgical cavity in order to repair the puncture wounds created by other endoscopic ports. It is also beneficial, however, to be able to use a camera to facilitate suturing of the puncture wound created by the endoscopic port that houses the camera. In order to do this during procedures utilizing certain conventional endoscopic ports, it is typically necessary to remove the endoscopic ports other than the one used for the camera and then position sutures in their associated puncture wounds. Prior to tying the suture to repair one of those wounds, an endoscopic port is often times re-inserted into the wound and the camera is removed from its endoscopic port and passed through the re-inserted endoscopic port to permit the surgeon to view the portion of the surgical cavity in which the endoscopic port from which the camera was removed is positioned. By using the endoscopic ports described herein, it is possible to position sutures in the patient for each of the puncture wounds without removing and re-inserting any of the associated endoscopic ports. The camera can simply be removed from its endoscopic port and positioned within one of the other endoscopic ports without removing and re-inserting any of those endoscopic ports. As a result, the repair of the puncture wound associated with the endoscopic port housing the camera can be greatly facilitated, while saving the time and risk associated with removing and re-inserting one or more of the endoscopic ports.

Other aspects, features, and advantages will be apparent from the description and drawings, and from the claims.

DESCRIPTION OF DRAWINGS

FIGS. 6A-6E schematically illustrate a method of using the kit of FIG. 5 to perform a laparoscopic surgical procedure.

DETAILED DESCRIPTION

Figure 1:
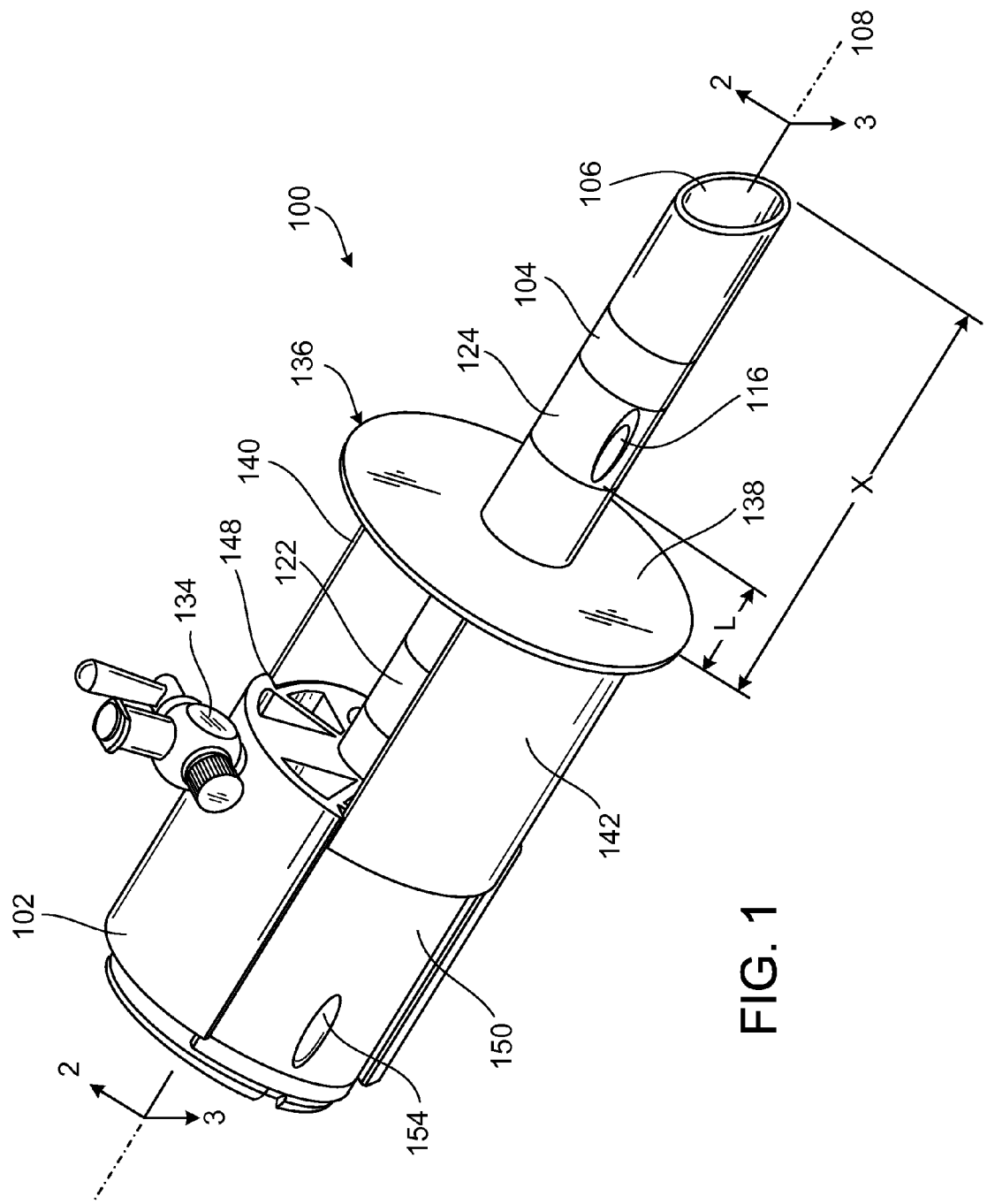
FIG. 1 is a perspective view of an endoscopic port that includes an axially displaceable stop ring located in a distal position along a cannula and that forms guide passageways for guiding a suture passer at a desired angle through the endoscopic port.
Figure 2:
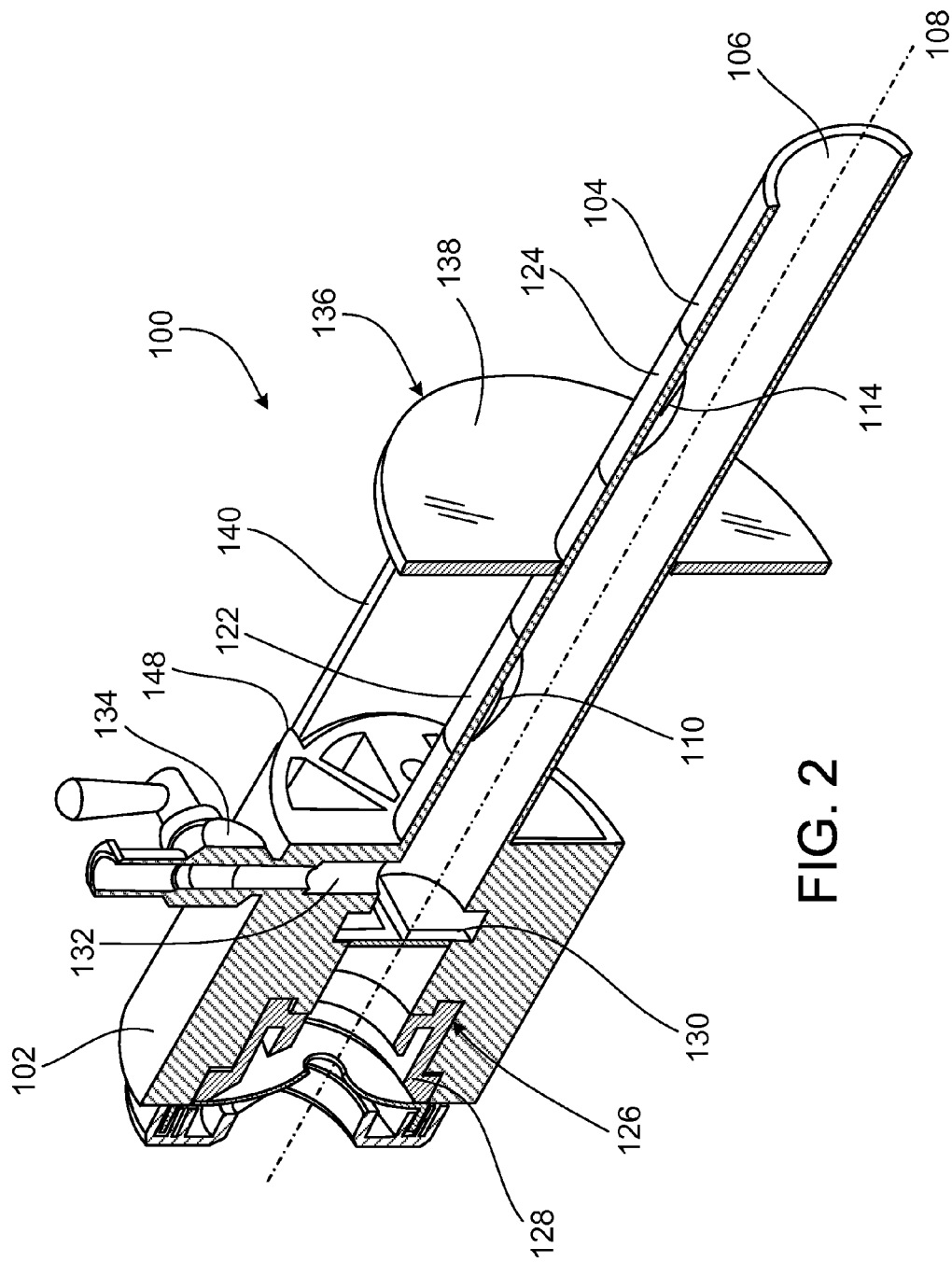
FIG. 2 is a cross-sectional perspective view of the endoscopic port of FIG. 1, taken along line 2-2 in FIG. 1.
Figure 3:
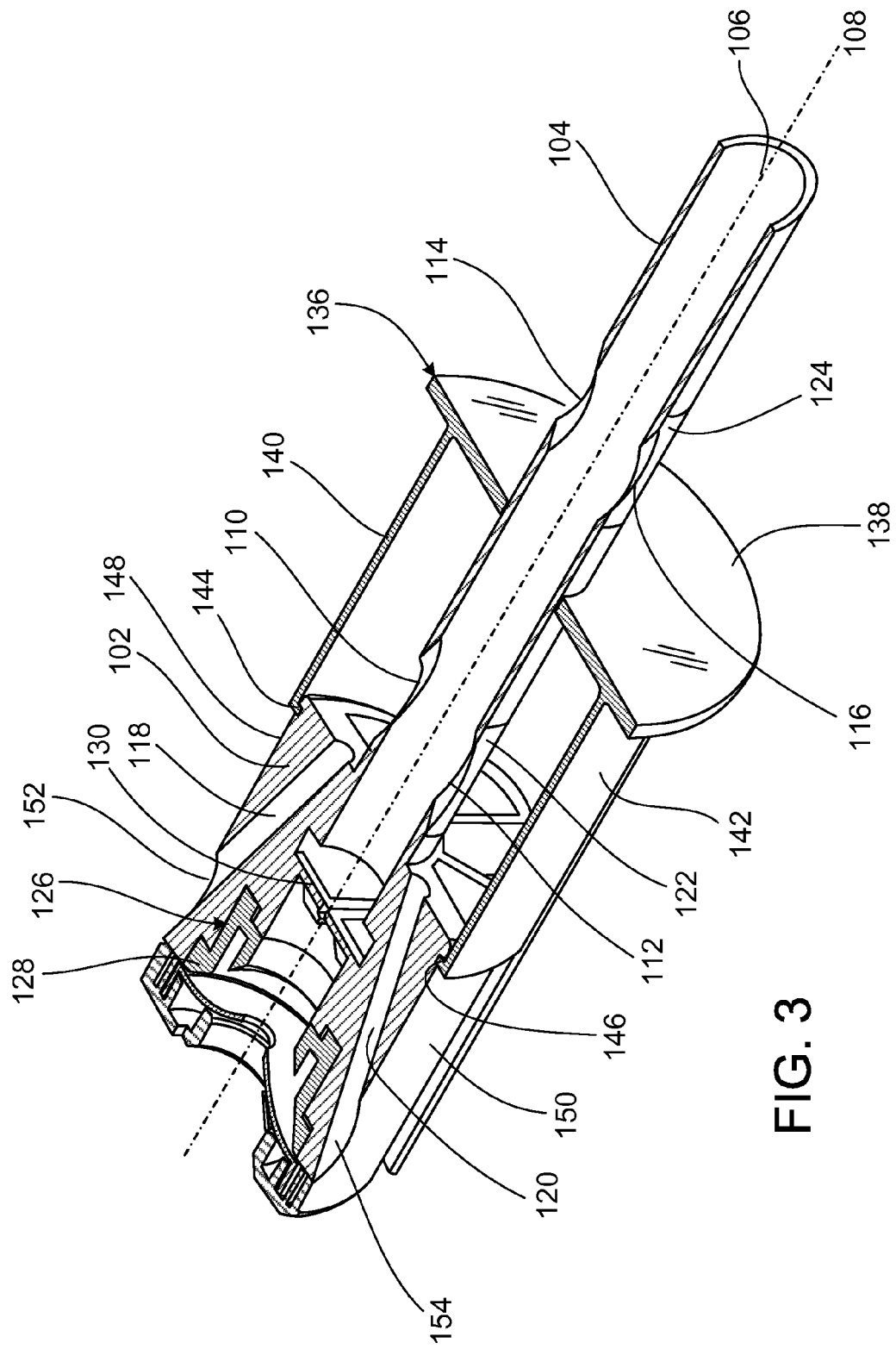
FIG. 3 is a cross-sectional perspective view of the endoscopic port of FIG. 1, taken along line 3-3 in FIG. 1.

As shown in FIGS. 1-3, an endoscopic port 100 includes a seal housing 102 attached to a proximal end region of a cannula 104. The cannula 104 includes a central lumen 106 that extends along a longitudinal axis 108 of the cannula 104 and is sized to receive one or more surgical instruments. In addition, the cannula 104 includes right and left proximal openings 110, 112 (partially shown in FIG. 3) and right and left distal openings 114, 116 (partially shown in FIG. 3) that extend through the side wall of the cannula 104 at an acute angle relative to the longitudinal axis 108. The seal housing 102 includes right and left guide channels 118, 120 (partially shown in FIG. 3) that similarly extend at an acute angle relative to the longitudinal axis 108. The right guide channel 118 aligns with the right proximal opening 110 and the left distal opening 116 such that a suture passer can be passed through a guide passageway formed by the right guide channel 118, the right proximal opening 110, and the left distal opening 116 during use. Similarly, the left guide channel 120 aligns with the left proximal opening 112 and the right distal opening 114 such that a suture passer can be passed through a guide passageway formed by the left guide channel 120, the left proximal opening 112, and the right distal opening 114 during use. As will be described in greater detail below, this arrangement permits a suture passer to be used to deliver a suture into a surgical cavity (e.g., abdominal cavity) of a patient and then retrieve the suture from the surgical cavity of the patient for repairing a puncture wound caused by the endoscopic port 100 while the endoscopic port 100 remains positioned within the puncture wound.

The angle at which the guide channels 118, 120 of the seal housing 102 and the openings 110, 112, 114, 116 of the cannula 104 extend can vary depending on the desired angle at which the suture passer is to pass through the tissue of the patient. This angle will dictate the distance between the suture and the puncture wound in which the endoscopic port 100 is positioned after the suture has been passed through the patient's tissue and into the surgical cavity. Typically, the guide channels 118, 120 and the openings 110, 112, 114, 116 extend at an angle of 8 degrees to 30 degrees (e.g., 12 degrees to 25 degrees, 16 degrees to 20 degrees, 16 degrees, 20 degrees, 25 degrees) relative to the longitudinal axis 108 of the cannula 104. However, the guide channels 118, 120 and the openings 110, 112, 114, 116 can alternatively extend at other acute angles relative to the longitudinal axis 108.

The guide channels 118, 120 and the openings 110, 112, 114, 116 typically extend through the seal housing 102 and the sidewall of the cannula 104 at substantially the same angle relative to the longitudinal axis 108. This helps to ensure a smooth passage of the suture passer through the passageways formed by the guide channels 118, 120 and the openings 110, 112, 114, 116. In addition, this geometry helps to ensure that the suture passer passes through the patient's tissue on either side of the puncture wound at the same angle and thus helps to ensure that the suture is spaced from the puncture wound by approximately the same distance on each side of the puncture wound. The quality and consistency of the repair of the puncture wound can be improved by using approximately equal spacing between the sutures and the puncture wound on either side of the puncture wound.

As shown in FIG. 1, heat shrink tubes 122, 124 are positioned around the portions of the cannula 104 that include the proximal and distal openings 110, 112, 114, 116. The heat shrink tubes 122, 124 are sealed to the cannula 104 in a substantially fluid-tight manner to ensure that fluid (e.g., insufflation gas) cannot escape from the central lumen 106 of the cannula 104 via the openings 110, 112, 114, 116 during the surgical procedures. In certain embodiments, the heat shrink tubes 122, 124 are opaque. The opacity of the heat shrink tubes 122, 124 can reduce (e.g., minimize) the amount of light (e.g., light emitted from operating room lights) allowed to pass into the surgical cavity via the openings during a surgical procedure. This can reduce the likelihood of undesired reflections picked up by a camera within the surgical cavity. The heat shrink tubes 122, 124 are formed of one or more materials that can be readily pierced by a suture passer. Examples of materials from which the heat shrink tubes 122, 124 can be formed include polyethylene terephthalate (PET), polytetrafluoroethylene (PTFE), polyetheretherketone (PEEK), polypropylene, and polyethylene.

As shown in FIGS. 2 and 3, a seal assembly 126 is located within the seal housing 102 of the endoscopic port 100. The seal assembly 126 includes a proximal seal 128 and a distal seal 130. The proximal and distal seals 128, 130 include openings that are positioned along the longitudinal axis 108 of the cannula 104 and are configured to receive a surgical instrument. The proximal seal 128 is designed to form a substantially fluid-tight seal with a surgical instrument when the instrument is disposed within the opening of the seal 128. The distal seal 130 is designed to form a substantially fluid-tight seal when no instrument is disposed in its opening. As shown in FIG. 3, the guide channels 118, 120 of the seal housing 102 are spaced from the seals 128, 130. Thus, the suture passer can be passed through the guide channels 118, 120 without interfering with the ability of the seals 128, 130 to provide the substantially fluid-tight sealing effect described above.

The seal housing 102, as shown in FIG. 2, also defines an insufflation lumen 132 that extends from the central lumen 106 of the cannula 104 to a valve 134 that is secured to the seal housing 102. During use, an insufflation gas pump can be connected to the valve 134 and operated with the valve 134 in the open position to cause insufflation gas to be delivered via the central lumen 106 of the cannula 104 to a surgical cavity in which the distal end of the cannula 104 is positioned. Other fluids can also be delivered to the surgical cavity in this way if desired.

Figure 4:
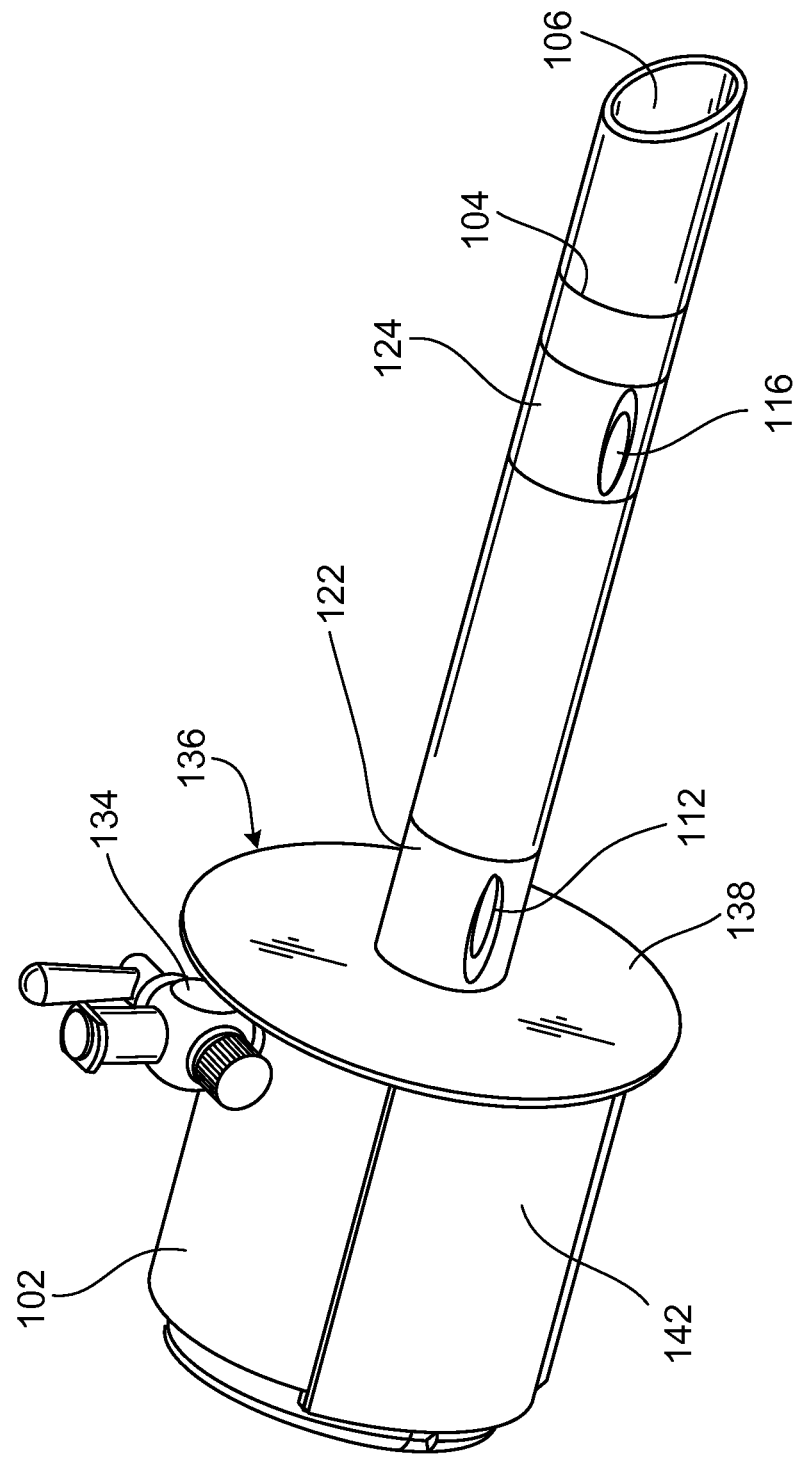
FIG. 4 is a perspective view of the endoscopic port of FIG. 1 with the stop ring located in a proximal position.

A stop ring 136 is slidably secured to the cannula 104 and can be axially moved relative to the cannula 104 between proximal and distal fixed positions. FIGS. 1-3 show the stop ring 136 in the distal position, while FIG. 4 shows the stop ring 136 in the proximal position. The stop ring 136 includes a ring-shaped plate 138 that encircles the cannula 104. The diameter of the plate 138 is typically about 3.0 mm to about 10 cm (e.g., about 1.0 cm to about 4.0 cm) greater than the diameter of the cannula 104 and is thus greater than the puncture wound to be created by the endoscopic port 100. As a result, the plate 138 cannot pass into the puncture wound during insertion of the endoscopic port 100 into the patient and instead abuts the outer skin surface of the patient. The flat, distal surface of the ring-shaped plate 138 can be pressed against the outer skin surface of the patient in a manner to control the depth to which the distal end of the cannula 104 penetrates the surgical cavity of the patient. Two resilient fingers or tabs 140, 142 extend proximally from the plate in a direction substantially parallel to the longitudinal axis 108 of the cannula 104. Projections 144, 146 (shown in FIG. 3) extend radially inward from proximal end regions of the fingers 140, 142.

Still referring to FIGS. 1-4, the seal housing 102 has recessed regions 148, 150 in which the fingers 140, 142 of the stop ring 136 are positioned and arranged to slide. The recessed regions 148, 150 of the seal housing 102 include proximal and distal depressions that are sized and shaped to receive the projections 144, 146 of the stop ring 136 to hold the stop ring 136 in proximal and distal positions along the cannula 104. The resiliency of the fingers 140, 142 forces the projections 144, 146 into the proximal depression when the stop ring 136 is in the proximal position and into the distal depression when the stop ring 136 is in the distal position. The fingers 140, 142 of the stop ring 136 cover entry ports 152, 154 (partially shown in FIG. 3) to the guide channels 118, 120 in the seal housing 102 when in the proximal position. When the stop ring 136 is locked in the distal position, the entry ports 152, 154 to the guide channels 118, 120 are exposed so that a suture passer can be guided through those channels.

When the stop ring 136 is in the distal position, as shown in FIG. 1, the distal surface of the stop ring 136 is positioned at a distance X from the distal tip of the cannula 104. This distance X typically exceeds an expected distance between an outer skin surface of the patient and an inner surface of a surgical cavity in which a surgical procedure is to be performed. This arrangement helps to ensure that the distal end of the cannula 104 extends slightly into the surgical cavity of the patient when the stop ring 136 is locked in the distal position and is pressed against the outer skin surface of the patient. A distance L between the distal surface of the stop ring 136 and the proximal ends of the distal openings 114, 116 in the cannula 104 is also a function of the patient's anatomy, in particular his or her body fat composition. The distance L and the angle at which the guide channels 118, 120 and the openings 110, 112, 114, 116 extend relative to the longitudinal axis of the cannula 104 are typically selected to ensure that a suture passer and suture can be passed through the tissue of the patient at a desired distance from the puncture wound in which the endoscopic port 100 is positioned.

The endoscopic port 100 can be provided in various different sizes, and the surgeon can select the one that fits best with the patient's anatomy. The distance X between the distal surface of the stop ring 136 and the distal end of the cannula 104 typically falls within the range of about 3.0 cm to about 12 cm. The distance L between the distal surface of the stop ring 136 and the distal openings 114, 116 in the cannula 104 can range from about 1.0 cm to about 5.0 cm. The overall length of the endoscopic port 100 typically ranges from about 5.0 cm to about 20 cm.

The components of the endoscopic port 100 can be formed of one or more of any of various different medical grade materials, including stainless steel, titanium, polycarbonate, Acrylonitrile butadiene styrene (ABS), polypropylene, acrylic, liquid crystal polymer (LCP), polyetheretherketone (PEEK), silicone, and thermoplastic elastomer (TPE). Typically, the cannula 104 and seal housing 102 are integrally molded with one another. However, these components can alternatively be formed separately and then attached (e.g., thermally bonded, adhesively bonded, or mechanically fastened) to one another.

Figure 5:
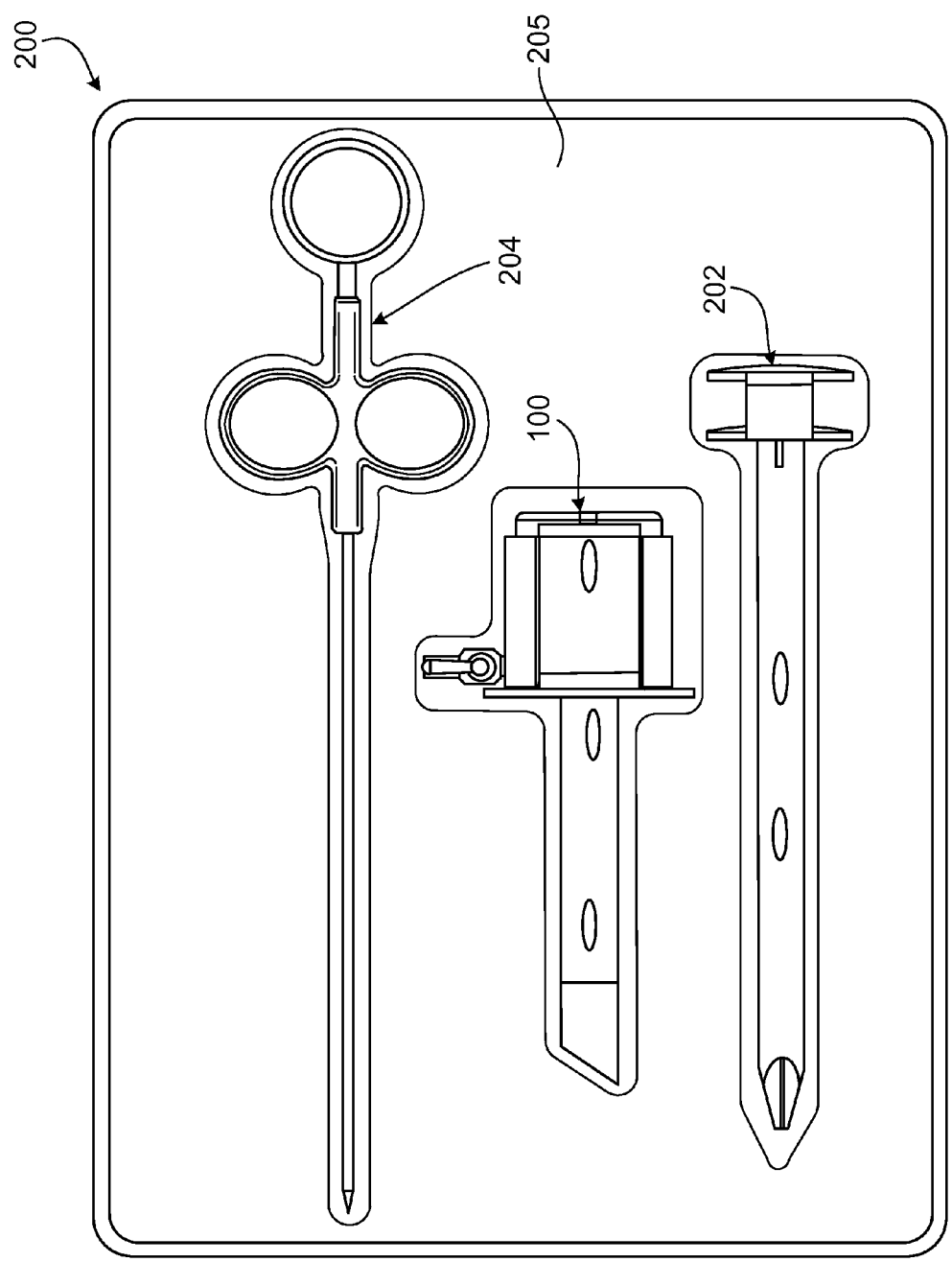
FIG. 5 is an endoscopic surgical kit that includes the endoscopic port of FIG. 1, an obturator, and a suture passer contained in recessed regions of a tray for storage and/or shipment.

FIG. 5 illustrates an endoscopic surgical kit 200 that includes the endoscopic port 100, an obturator 202, and a suture passer 204 positioned in recessed cavities formed in a carrying tray 205. The obturator 202 and the suture passer 204 can be any of various suitably sized obturators and suture passers. An example of a suitable suture passer is the Carter-Thomason suture passer, available from CooperSurgical, Inc. (Trumbull, Conn.). While the kit 200 is illustrated as including only a single endoscopic port, obturator, and suture passer, the kit can alternatively include multiple different endoscopic ports, obturators, and/or suture passers of varying size to enable endoscopic (e.g., laparoscopic) surgical procedures to be performed on patients of various different sizes.

Figure 6A:
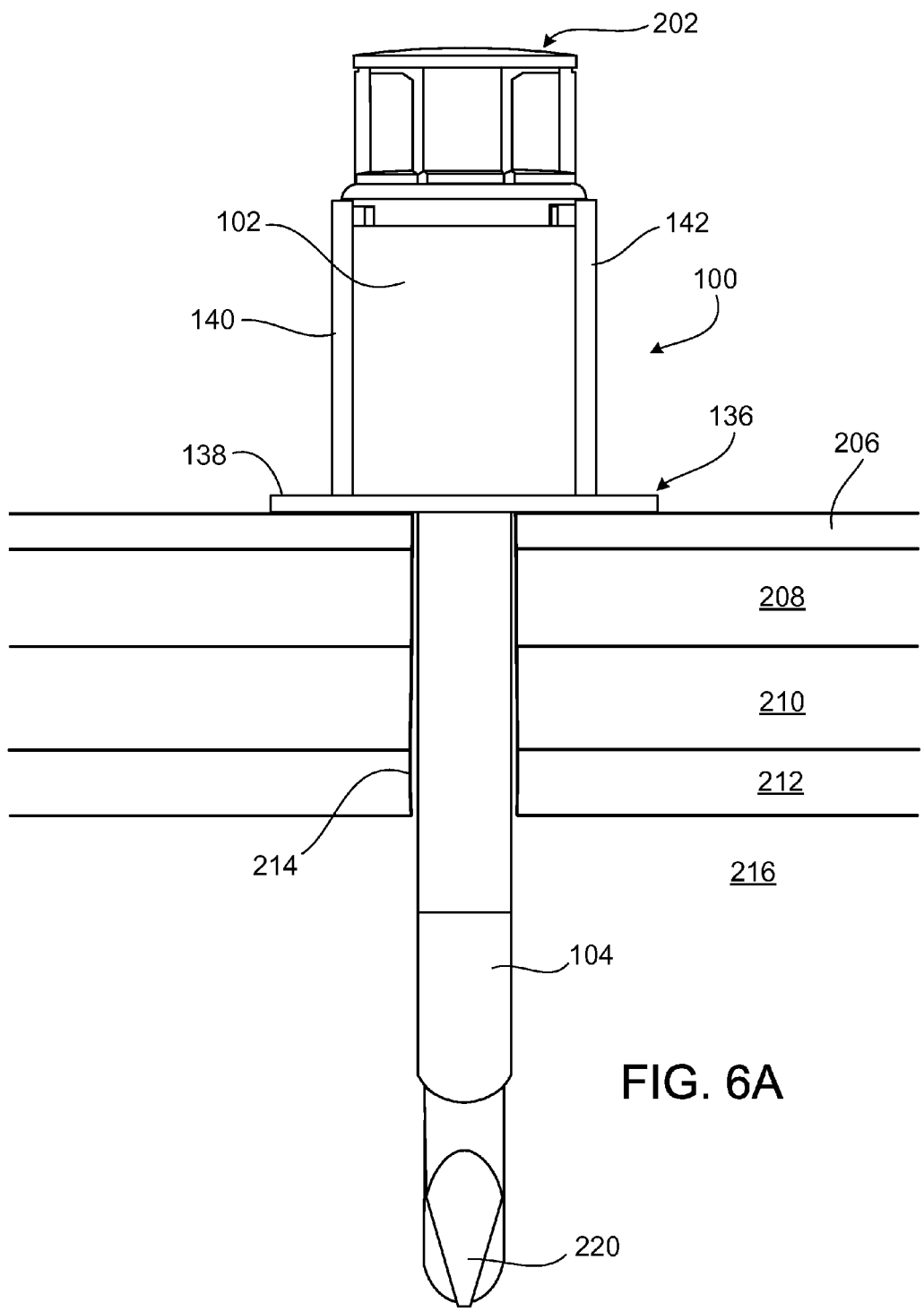

FIGS. 6A-6E schematically illustrate a method of using the kit 200 to perform a laparoscopic surgical procedure. Referring to FIG. 6A, the obturator 202 is first inserted into the central lumen 106 of the endoscopic port 100 and then the endoscopic port 100 and obturator 202 are together inserted through the patient's skin 206, muscle 208, fascia 210, and peritoneum 212, thereby forming a puncture wound 214 in the patient's tissue. The endoscopic port 100 and obturator 202 are advanced until the distal surface of the stop ring 136, which is fixed in the proximal position at this point, contacts the outer skin surface surrounding the puncture wound 214. In this position, the proximal portion of the cannula 104 sits within the puncture wound 214, and the distal end of the cannula 104 and the sharp, distal tip 220 of the obturator 202 are positioned in the abdominal cavity 216 of the patient.

Figure 6B:
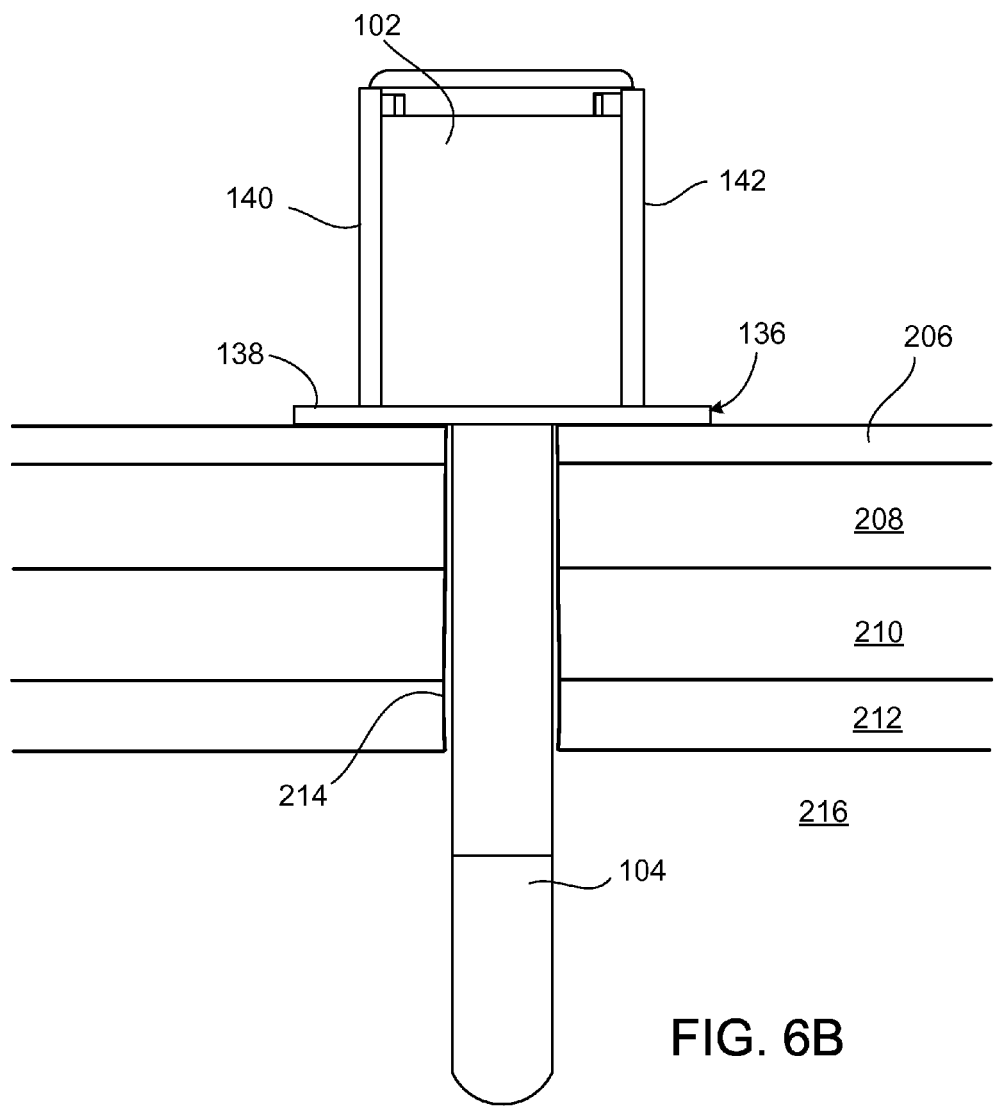

As shown in FIG. 6B, after positioning the distal end of the cannula 104 as desired within the abdominal cavity 216, the obturator 202 is removed from the endoscopic port 100, thereby freeing the central lumen 106 to receive other types of surgical instruments. If the abdominal cavity 216 has not yet been insufflated, a fluid pump is then connected to the valve 134 of the endoscopic port 100 and operated to insufflate the abdominal cavity 216 to a desired pressure, i.e., to produce a pneumoperitoneum. The valve 134 is then closed. The closed valve 134, the seal assembly 126 in the seal housing 102, and the heat shrink tubes 122, 124 over the openings 110, 112, 114, 116 in the cannula 104 all serve to maintain this pneumoperitoneum. One or more surgical instruments are then inserted through the central lumen 106 of the endoscopic port 100 and into the abdominal cavity 216 to perform the surgical procedure while the pneumoperitoneum is maintained.

After completing the procedure in the abdominal cavity 216, all surgical instruments are removed from the endoscopic port 100. Referring to FIG. 6C, the user then holds the stop ring 136 against the outer skin surface of the patient while retracting the cannula 104 and the seal housing 102 proximally relative to the stop ring 136. The cannula 104 and seal housing 102 are retracted until the stop ring 136 becomes locked in its distal position. In this state, the distal openings 114, 116 in the cannula 104 are positioned within the tissue layers of the patient.

Figure 6D:
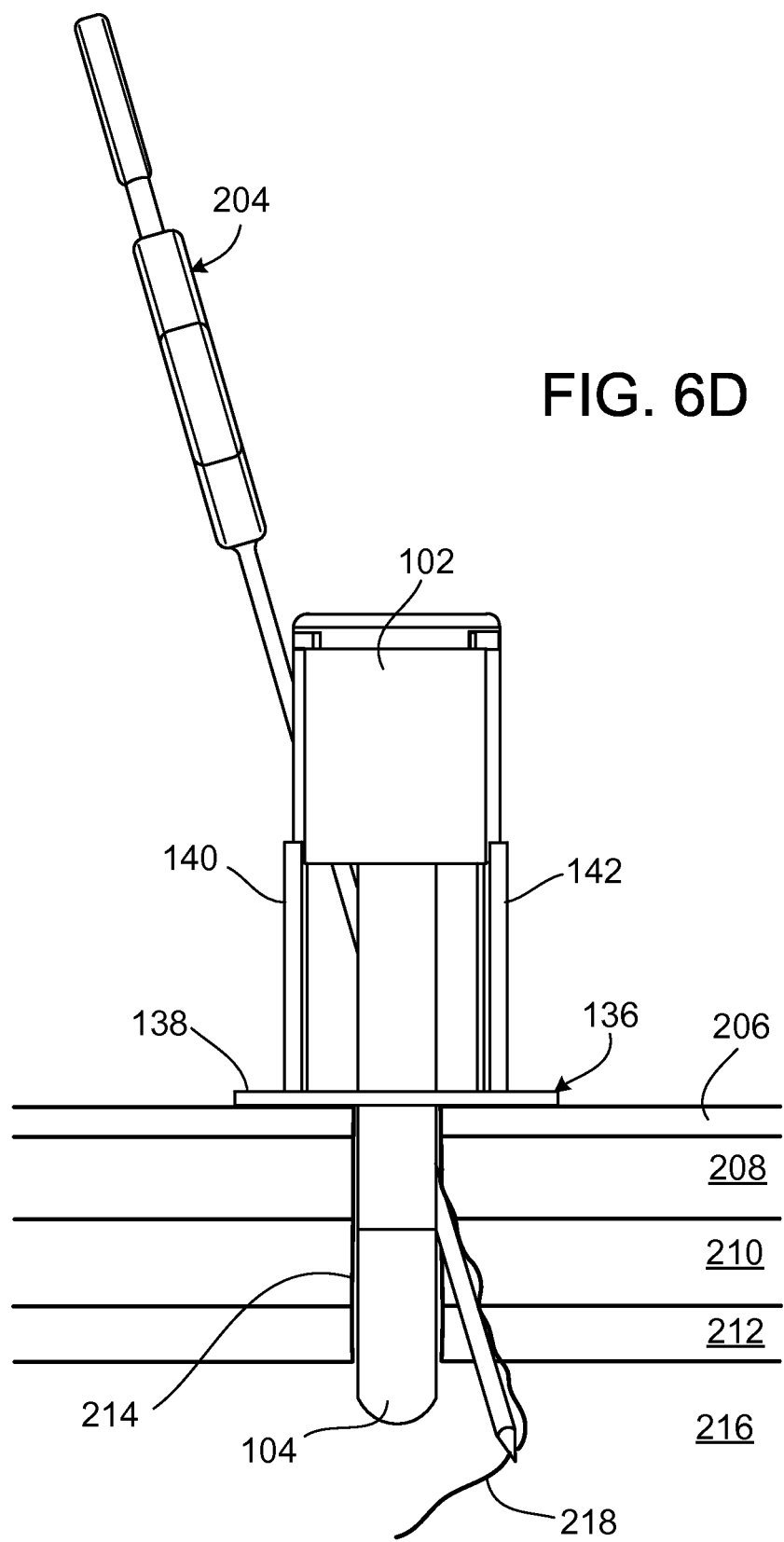

As shown in FIG. 6D, the suture passer 204 is then inserted with a suture 218 in its grasp through the guide channel 118 of the seal housing 102 and through the proximal and distal openings 110, 116 of the cannula 104. The surgeon then forces the suture passer 204 and the grasped suture 218 through the peritoneum 212 and into the abdominal cavity 216. As discussed above, due to the orientation of the guide channel 118 and the openings 110, 116, the suture passer 204 passes through the tissue of the patient at a desired angle (e.g., between 8 degrees and 30 degrees) relative to the longitudinal axis 108 so that a desired amount of tissue remains between the puncture wound 214 and the suture 218. In certain embodiments, a distance of about 2.0 mm to about 20 mm remains between the suture 218 and the cannula 104 in the peritoneum. The insertion of the suture 218 into the abdominal cavity 216 in this manner is typically viewed via video generated by a camera inserted into the abdominal cavity 216 via another endoscopic port positioned in the patient. After positioning the suture 218 within the abdominal cavity 216, the suture 218 is released from the suture passer 204 and the suture passer 204 is removed from the endoscopic port 100.

Referring to FIG. 6E, the suture passer 204 is then re-inserted with no suture in its grasp through the guide channel 120 of the seal housing 102 and the proximal and distal openings 112, 114 of the cannula 104 and into the abdominal cavity 216 in much the same way as described above. With the aid of the video generated by the camera positioned in the other endoscopic port, the surgeon uses the suture passer 204 to grasp the suture 218 and then pulls the suture passer 204 and the grasped suture 218 out of the endoscopic port 100 via the guide channel 120 and the openings 112, 114.

Before tying the suture 218 to close the puncture wound 214, a suture can also be positioned in the tissue surrounding the puncture wound caused by the endoscopic port dedicated to the camera. To do this, the camera is removed from its endoscopic port and inserted into the endoscopic port 100 discussed above. The same procedure described above is then used to position a suture in preparation for closing the puncture wound formed by the endoscopic port that originally contained the camera. Once that is complete, the endoscopic ports are withdrawn from their associated puncture wounds, and the sutures are tied to repair those puncture wounds. Due to the size and geometry of each endoscopic port and the guide channels and openings defined by each endoscopic port, the fascia and peritoneum are encompassed in a relatively smooth mass closure under the skin to produce a high quality repair.

The surgical procedure described above can typically be carried out in less time than surgical procedures that require endoscopic ports to be removed from their puncture wounds and replaced by separate guide members that are used to properly place the sutures. In addition, the surgical procedure described above typically result in improved placement of the sutures as compared to surgical procedures that utilize no guide member for placing the sutures.

Figure 7:
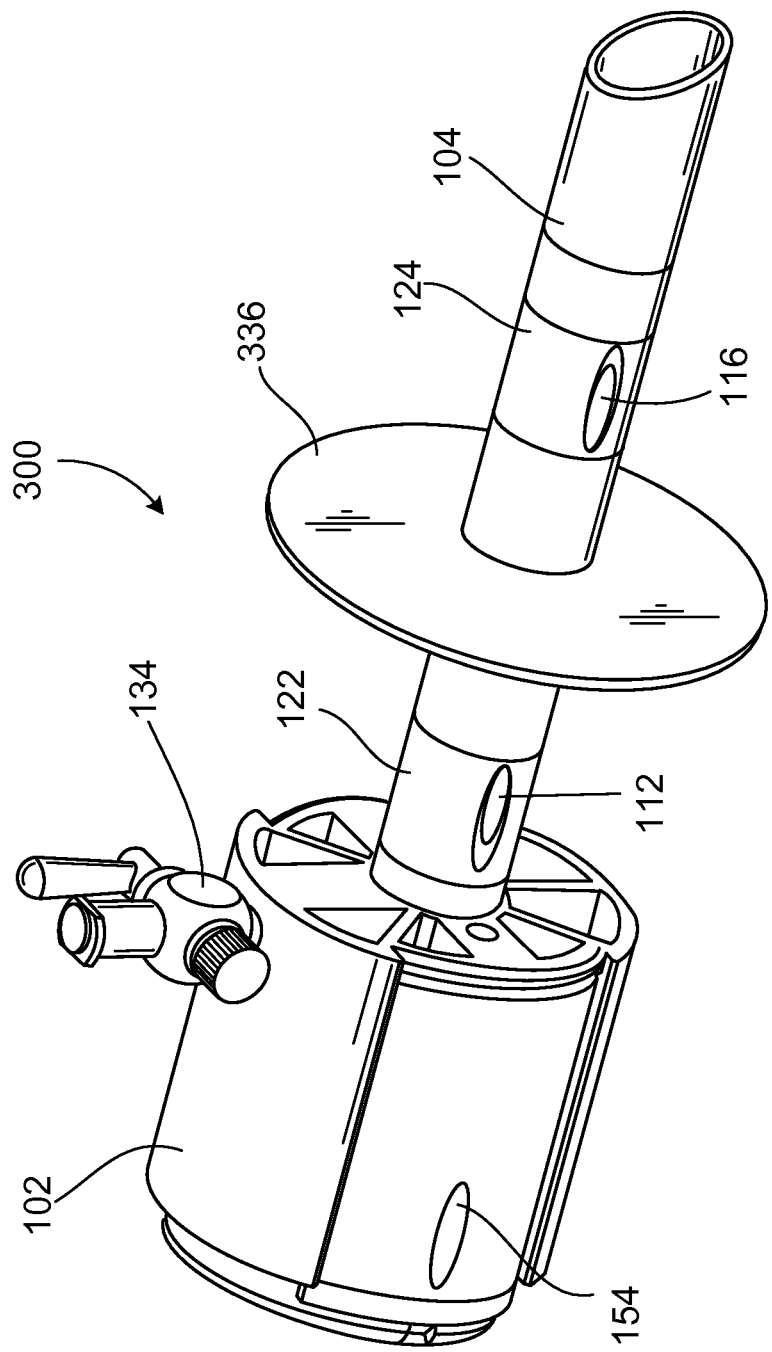
FIG. 7 is a perspective view of an endoscopic port that includes a plate that is axially fixed with respect to a cannula.

While certain embodiments have been described, other embodiments are possible. For example, while the stop ring 136 has been described as being axially displaceable along the cannula 104, a stationary stop can alternatively be used. As shown in FIG. 7, for example, an endoscopic port 300 has a ring-shaped plate 336 that is attached (e.g., thermally bonded, adhesively bonded, or mechanically coupled) to the cannula 104. The position of the plate 336 along the cannula 104 generally corresponds to the distal position of the stop ring 136 along the cannula 104 of the endoscopic port 100 described above. The endoscopic port 300 can be used in much the same way as the endoscopic port 100. However, due to the axially fixed placement of the ring-shaped plate 336 on the cannula 104, the ring-shaped plate 336 cannot be moved to a proximal position. As a result, the cannula 104 of the endoscopic port 300 typically cannot be extended as far into the abdominal cavity of the patient as the cannula 104 of the endoscopic port 100.

While the stationary stop ring has been described as being positioned at a location that generally corresponds to the distal position of the stop ring 136 along the cannula 104 of the endoscopic port 100, the stop ring can alternatively positioned at other locations along the cannula 104. In certain embodiments, for example, the stop ring is substantially flush with distal end of the seal housing 102. In such embodiments, the stop ring can be integrally molded with the seal housing 102. The guide openings in the cannula may be located at different positions along the cannula depending on the location of the stop ring.

Figure 8:
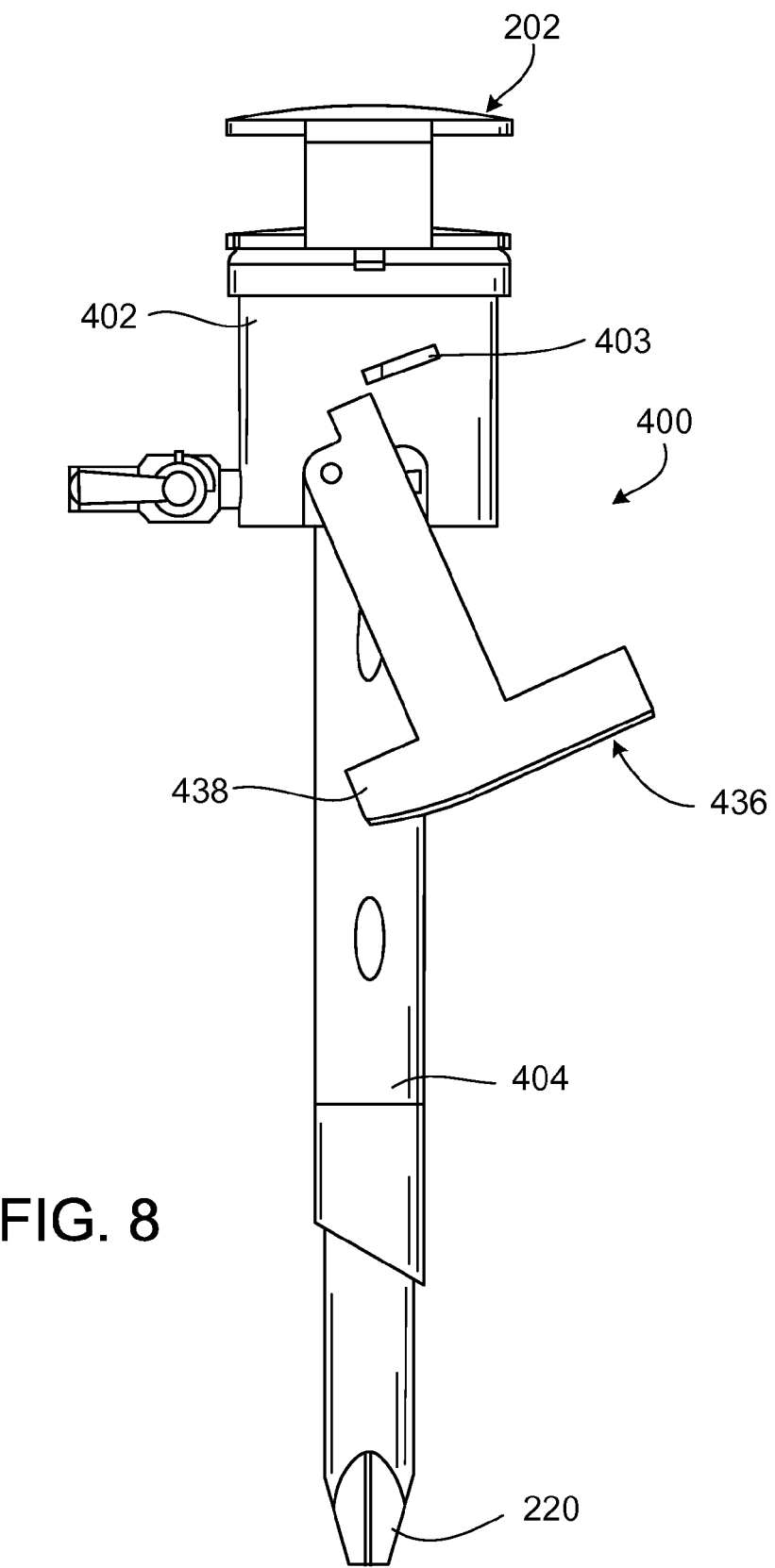
FIG. 8 is a front view of a trocar including an obturator positioned in an endoscopic port that includes a stop member that is pivotable relative to a cannula.

While the stop ring 136 and the plate 336 have been described as being axially displaceable along the cannula or axially fixed relative to the cannula, in some embodiments, a stop member is pivotably secured to the cannula. As shown in FIG. 8, for example, an endoscopic port 400 includes a stop member 436 that is pivotably attached to a seal housing 402 from which a cannula 404 extends. The stop member 436 can be pivoted between a distal position and a proximal position. A projection 403 extends from the outer surface of the seal housing 402 and engages a latch of the stop member 436 when the ring-shaped member 436 is moved to the proximal position in order to lock the stop member 436 in the proximal position. When a sufficient pivot force is applied to the stop member 436, it can be moved from the proximal position to the distal position. A generally ring-shaped or c-shaped plate 438 of the stop member 436 includes a void that receives the cannula 404 when the ring-shaped member 436 is in the distal position. The left lower surface of the plate 438 (from the perspective shown in FIG. 8) is chamfered or rounded to prevent the plate 438 from lifting the endoscopic port 400 farther than desired away from the skin surface of the patient when the ring-shaped member is rotated from the proximal position to the distal position. The endoscopic port 400 can be used in much the same way as the endoscopic port 100 discussed above. However, after completing the surgical procedure within the surgical cavity, the stop member 436 is pivoted from the proximal position to the distal position, rather than being axially displaced from the proximal position to the distal position, to position the distal end of the cannula 104 so that it only slightly protrudes into the surgical cavity.

Figure 9:
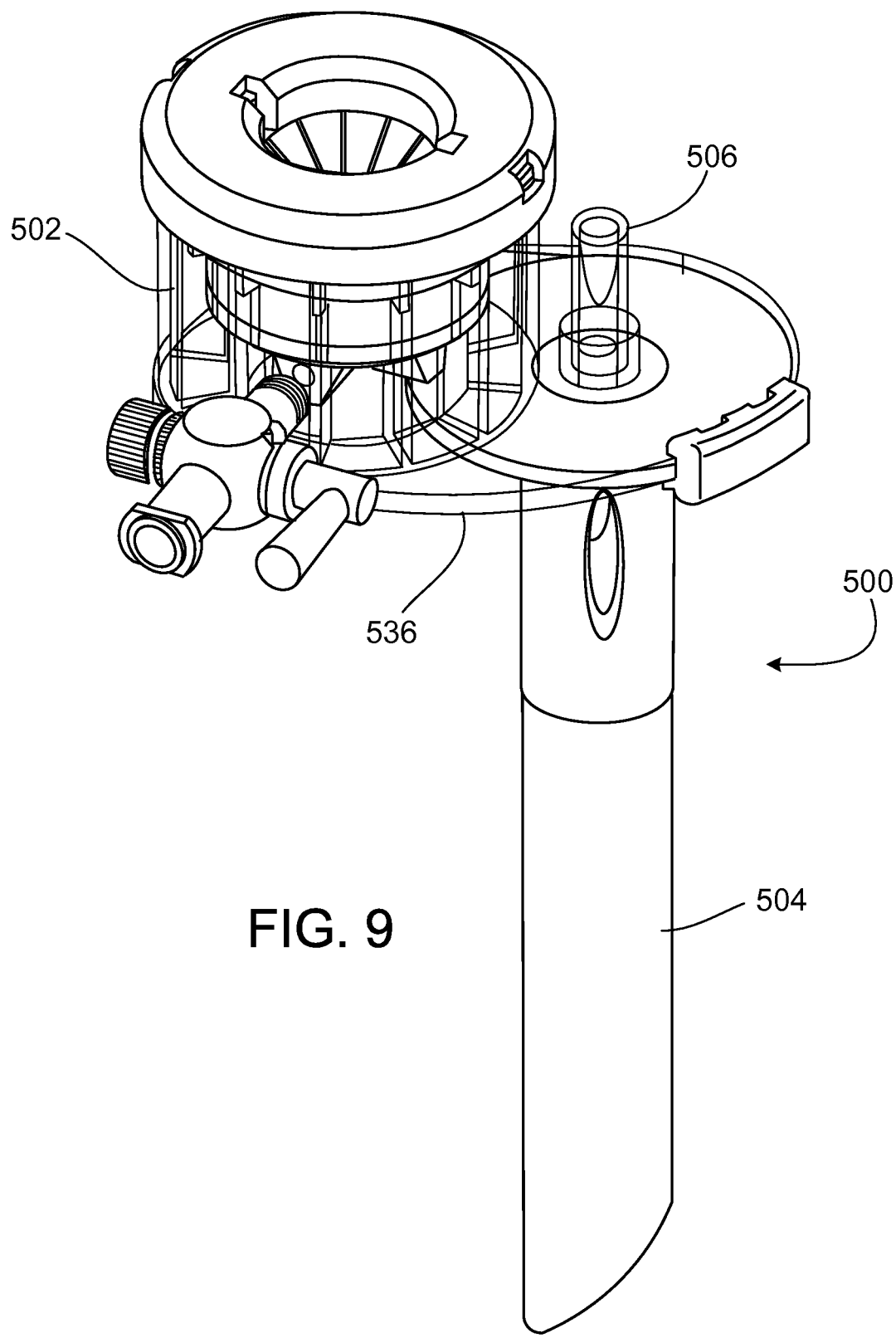
FIG. 9 is a top, perspective view of an endoscopic port that includes a rotatable platform positioned atop a cannula for aligning either a guide stem of a seal housing with the cannula.

FIG. 9 illustrates another endoscopic port 500 that includes a platform 536 that is pivotably attached to a cannula 504. A seal housing 502 is attached to one region of platform 536 while a guide stem 506 is attached to another region of the platform 536. When it is desired to insert surgical instruments through the central lumen of the cannula 504, the platform is pivoted so that the seal housing 502 is positioned above and aligned with the cannula 504. In this position, the seal housing 502 functions in much the same way as the seal housing 102 of the endoscopic port 100 described above. When it is desired to guide a suture passer though the endoscopic port 500 in order to place a suture in the patient, the platform 536 is pivoted so that the guide stem 506 is positioned above and aligned with the cannula 504. The guide stem 506 includes passages that align with openings along the cannula 504 to guide the suture passer and suture into the patient's tissue at a desired angle.

While guide channels have been described as being formed in the seal housing of certain endoscopic ports discussed above, in some embodiments, an endoscopic port includes a guide insert that defines the guide channels and can be disposed within the seal housing in place of the seal assembly. For example, during a surgical procedure, the seal assembly can be positioned within the seal housing in much the same way as described above. After completing the procedure, the seal assembly can be replaced by the guide insert to provide a guiding function for the suture passer. For example, the seal housing can include a hinged or pivotable top that can be opened to permit the seal assembly to be removed and replaced with the guide insert. Alternatively, the guide insert can be configured to be disposed in the openings of the seals of the seal assembly. In such cases, there is no need to remove the seal assembly from the seal housing. The guide channels of the guide insert align with one or more openings in the cannula of the endoscopic port in much the same way as described above with respect to other endoscopic ports. Due to the containment of the plug within the seal housing, this endoscopic port can be more slender than many of the endoscopic ports described above.

While the endoscopic ports above have been described as being used with a single suture passer that is first extended through one guide passageway of the endoscopic port and then removed and extended through the other guide passageway of the endoscopic port, in some embodiments, the guide passageways of the endoscopic port are configured so that a first suture passer can be disposed within one passageway while a second suture passer is disposed within another passageway. This can help to reduce the amount of gas that escapes from the surgical cavity via the openings during the procedure and thus helps to maintain a desired pressure within the surgical cavity.

While some of the endoscopic ports discussed above have been described as including multiple guide passageways through which a suture passer can be passed, in certain embodiments, only one such passageway is provided. In those embodiments, the endoscopic port can be rotated 180 degrees after inserting the suture into the abdominal cavity and before retrieving the suture to ensure proper placement of the suture on each side of the puncture wound.

While the openings in the cannula have been described as being covered and sealed by heat shrink tubing, other techniques can be used. For example, film patches or stickers can be bonded or adhered over the openings. Alternatively or additionally, a seal can cover each of the openings in a manner to create a fluid-tight self-seal when no suture passer is positioned in the opening and to create a seal around the suture passer when the suture passer is positioned in the opening. Such a seal can, for example, be formed of silicone or a thermoplastic elastomer (TPE).

While a member covers the openings in each of the embodiments described above, in some embodiments, no covering is used for the openings.

Certain methods above involve connecting a fluid pump to a valve of the endoscopic port and then, after insufflating the abdominal cavity to a desired pressure, closing the valve. However, in some embodiments the fluid pump is connected to the valve of an endoscopic port and the fluid pump remains running throughout the procedure. In such embodiments, that one endoscopic port is typically dedicated to insufflation of the surgical cavity while other endoscopic ports are used as conduits for passing surgical instruments into the surgical cavity. The endoscopic ports used as conduits for the surgical instruments may be of identical construction to the endoscopic port dedicated to insufflation. The valves of the endoscopic ports used for passing surgical instruments into the surgical cavity will remain closed during the procedure to help prevent a pressure loss in the surgical cavity.

While the endoscopic ports discussed above have been primarily described as being used to perform laparoscopic procedures in abdominal cavities of patients, it should be understood that the endoscopic ports can also be used to perform any of various other endoscopic surgical procedures.

Other embodiments are within the scope of the following claims.

What is claimed is:

1. An endoscopic port comprising:
an elongate cannula defining a central lumen that extends substantially parallel to a longitudinal axis of the cannula, the central lumen being sized to receive at least one surgical instrument, a sidewall of the cannula defining a first opening that extends at an acute angle relative to the longitudinal axis of the cannula, the first opening being sized to receive a suture passer; and
a stop member secured to the cannula and configured to contact an outer skin surface of a patient, the stop member being displaceable away from a seal housing attached to the cannula to a distal position along the cannula in which a first portion of the cannula is covered lengthwise by the stop member, and the stop member being displaceable toward the seal housing to a proximal position along the cannula in which a second, shorter portion of the cannula is covered lengthwise by the stop member,
wherein the stop member is configured to be releasably locked in the proximal and distal positions, the stop member comprises a projection and the endoscopic port defines proximal and distal depressions configured to receive the projection when the stop member is in the proximal and distal positions, respectively, and the stop member comprises a resilient tab from which the projection extends.

2. The endoscopic port of claim 1, wherein the sidewall of the cannula further defines a second opening that is longitudinally spaced from the first opening and extends at an acute angle relative to the longitudinal axis of the cannula, the first and second openings being aligned so that a suture passer can be simultaneously disposed within the first and second openings.

3. The endoscopic port of claim 2, wherein the sidewall of the cannula further defines third and fourth openings that are longitudinally spaced from one another and extend at an acute angle relative to the longitudinal axis of the cannula, the third and fourth openings being aligned so that a suture passer can be simultaneously disposed within the third and fourth openings.

4. The endoscopic port of claim 3, wherein each of the first, second, third, and fourth openings extends at substantially the same angle relative to the longitudinal axis.

5. The endoscopic port of claim 1, wherein the first opening extends through the sidewall of the cannula at an angle of 8 degrees to 30 degrees relative to the longitudinal axis.

6. The endoscopic port of claim 1, wherein the stop member has a width greater than a width of the cannula.

7. The endoscopic port of claim 6, wherein the stop member has a substantially flat surface configured to abut the outer skin surface of the patient when the endoscopic port is inserted into a surgical cavity of the patient.

8. The endoscopic port of claim 7, wherein a distance between the flat surface of the stop member and a distal tip of the endoscopic port is greater than a distance between the outer skin surface of the patient and the surgical cavity.

9. The endoscopic port of claim 6, wherein the stop member is a ring having a diameter greater than an outer diameter of the cannula.

10. The endoscopic port of claim 1, wherein the stop member covers the first opening when the stop member is in the distal position and the stop member does not cover the first opening when the stop member is in the proximal position.

11. The endoscopic port of claim 1, wherein a distance between a distal surface of the stop member and a distal tip of the endoscopic port is greater than a distance between the outer skin surface of the patient and a surgical cavity into which the endoscopic port is to be inserted.

12. The endoscopic port of claim 1, wherein the depressions are formed in the seal housing attached to the cannula.

13. The endoscopic port of claim 1, wherein the stop member is axially displaceable between the proximal and distal positions.

14. The endoscopic port of claim 1, wherein the endoscopic port defines a second opening that is longitudinally spaced from the first opening and extends at an acute angle relative to the longitudinal axis of the cannula, the first and second openings being aligned so that a suture passer can be simultaneously disposed within the first and second openings.

15. The endoscopic port of claim 14, wherein the second opening is defined by the cannula.

16. The endoscopic port of claim 14, wherein the second opening is defined by the seal housing attached to the cannula.

17. The endoscopic port of claim 16, wherein the stop member covers the second opening when the stop member is in the proximal position, and the stop member does not cover the second opening when the stop member is in the distal position.

18. The endoscopic port of claim 1, further comprising a pierceable material secured to the cannula in a manner such that the pierceable material covers the first opening.

19. The endoscopic port of claim 18, wherein the pierceable material forms a fluid-tight seal with the cannula.

20. The endoscopic port of claim 1, wherein the stop member extends radially outward from the cannula, such that the stop member abuts the outer skin surface of the patient when the endoscopic port is inserted into a surgical cavity of the patient.

21. The endoscopic port of claim 1, wherein the stop member is slidable along the seal housing.

22. The endoscopic port of claim 1, wherein the seal housing is attached to a proximal end region of the cannula.

23. An endoscopic surgical kit comprising:
a suture passer;
an endoscopic port comprising an elongate cannula defining a central lumen that extends substantially parallel to a longitudinal axis of the cannula, the central lumen being sized to receive a surgical instrument, a sidewall of the cannula defining a first opening that extends through the sidewall of the cannula at an acute angle relative to the longitudinal axis of the cannula, the first opening being sized to receive the suture passer; and
a stop member secured to the cannula and configured to contact an outer skin surface of a patient, the stop member being displaceable away from a seal housing attached to the cannula to a distal position along the cannula in which a first portion of the cannula is covered lengthwise by the stop member, and the stop member being displaceable toward the seal housing to a proximal position along the cannula in which a second, shorter portion of the cannula is covered lengthwise by the stop member,
wherein the stop member is configured to be releasably locked in the proximal and distal positions, the stop member comprises a projection and the endoscopic port defines proximal and distal depressions configured to receive the projection when the stop member is in the proximal and distal positions, respectively, and the stop member comprises a resilient tab from which the projection extends.

24. The endoscopic surgical kit of claim 23, further comprising an obturator configured to be disposed within the central lumen of the cannula.

25. The endoscopic surgical kit of claim 23, wherein the kit comprises a plurality of differently sized endoscopic ports.

26. A method comprising:
inserting an endoscopic port and an obturator into a patient thereby forming a puncture wound, wherein said obturator is disposed within a central lumen of a cannula, and the endoscopic port is inserted until a stop member that is displaceably secured to the cannula contacts an outer skin surface of the patient, the stop member being secured in a proximal position along the cannula in which a first portion of the cannula is covered lengthwise by the stop member, and in which a distal end of the stop member is positioned adjacent an end of a seal housing attached to the cannula;
removing the obturator from the central lumen of the cannula;
retracting the cannula with respect to the stop member until the stop member is secured in a distal position along the cannula in which a second, longer portion of the cannula is covered lengthwise by the stop member, and in which the distal end of the stop member is spaced apart from the end of the seal housing; and
with the endoscopic port disposed within the puncture wound, passing a suture through the endoscopic port and through tissue of the patient adjacent the endoscopic port.

* * * * *

UNITED STATES PATENT AND TRADEMARK OFFICE
CERTIFICATE OF CORRECTION

| | | |
|---|---|---|
| PATENT NO. | : 8,979,747 B2 | Page 1 of 1 |
| APPLICATION NO. | : 13/555660 | |
| DATED | : March 17, 2015 | |
| INVENTOR(S) | : Robert D. Auerbach, Charles Sherts and Robert Williams | |

It is certified that error appears in the above-identified patent and that said Letters Patent is hereby corrected as shown below:

<u>Title Page: Item 73</u>

Column 1 (Assignee), Line 1, delete "Cooper Surgicalk, Inc.," and insert -- CooperSurgical, Inc., --

Signed and Sealed this
Fourteenth Day of July, 2015

Michelle K. Lee
*Director of the United States Patent and Trademark Office*